United States Patent [19]
Jung et al.

[11] 3,932,496
[45] Jan. 13, 1976

[54] MONO- AND DIALKYLATED PROSTYNOIC ACID DERIVATIVES

[75] Inventors: Christopher Jung, Morton Grove; Raphael Pappo, Skokie, both of Ill.

[73] Assignee: G. D. Searle & Co., Chicago, Ill.

[22] Filed: Apr. 23, 1973

[21] Appl. No.: 353,216

[52] U.S. Cl.... 260/514 D; 260/345.9; 260/410.9 R; 260/413; 260/448 A; 260/468 D; 260/471 R; 260/475 R; 260/488 R; 260/632 Y; 424/305; 424/317

[51] Int. Cl.[2].................. C07C 61/38; C07C 61/74

[58] Field of Search......... 260/468 D, 514 D, 488 R

[56] References Cited
UNITED STATES PATENTS
3,787,449  1/1974  Collins et al..................... 260/345.7

OTHER PUBLICATIONS

Pappo et al., Annals of N.Y. Academy of Sciences, Vol. 180, (1971).

Robert, Research in Prostaglandins, 2, No. 4, (1973).

*Primary Examiner*—Robert Gerstl
*Attorney, Agent, or Firm*—Elliot N. Schubert; John A. Dhuey

[57] ABSTRACT

Novel mono- and dialkylated prostynoic acid derivatives, prepared by condensation of a suitably substituted cyclopentene carboxylic acid or ester with a suitable organometallic alkynyl derivative, display valuable pharmacological properties. For example, they are potent inhibitors of gastric secretion.

7 Claims, No Drawings

MONO- AND DIALKYLATED PROSTYNOIC ACID DERIVATIVES

The present invention relates to novel mono- and dialkylated prostynoic acid derivatives as represented by the following structural formula

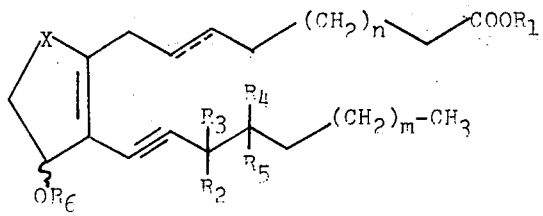

wherein $R_1$ is hydrogen or a lower alkyl radical, $R_2$ represents hydrogen or a hydroxy or lower alkanoyloxy radical, $R_3$ denotes hydrogen or a lower alkyl radical, $R_5$ is a $R_4$ can be hydrogen or a lower alkyl radical, $R_5$ is a lower alkyl radical, or $R_4$ and $R_5$ together or $R_3$ and $R_4$ together comprise the residue of a cycloalkyl group containing 3–12 carbon atoms, $R_6$ can be hydrogen or a lower alkanoyl radical, X denotes a carbonyl, hydroxymethylene or (lower alkanoyl)oxymethylene radical, $n$ is 1 or 2, $m$ is a positive integer less than 5, the dotted line indicates an optional double bond, alternatively in the cis or trans configuration, and the wavy line indicates the alternative R and S stereochemical configuration.

A preferred embodiment of the present invention consists of the novel compounds represented by the following structural formula

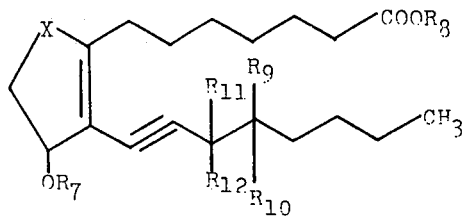

wherein $R_7$ is hydrogen or a lower alkanoyl radical, $R_8$ is hydrogen or a lower alkyl radical, $R_9$ is hydrogen or a lower alkyl radical, $R_{10}$ is a lower alkyl radical, $R_{11}$ is hydrogen or a lower alkanoyl radical and $R_{12}$ is hydrogen or a lower alkyl radical.

The lower alkyl radicals embraced in the foregoing structural formulae are typified by methyl, ethy, propyl, butyl, pentyl, hexyl, heptyl and the branched-chain radicals isomeric therewith.

The lower alkanoyl radicals denoted in those formulae are exemplified by formyl, acetyl, propionyl, butyryl, valeryl, caproyl, heptanoyl, and the corresponding branched-chain isomers.

The cycloalkyl radicals encompassed by the preceding structural formulae are typified by cyclopropyl, cyclohexyl, clyclooctyl, cyclododecyl, etc.

The compounds of the present invention are conveniently manufactured by the condensation of a suitably substituted cyclopentene carboxylic acid or ester of the types described in U.S. Pat. No. 3,558,682, issued Jan. 26, 1971 and in Bruhn and Pappo U.S. Pat. application Ser. No. 346,358, filed Mar. 30, 1973, with a suitable acetylenic derivative as represented by the following structural formula

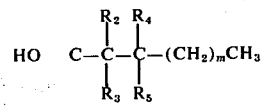

wherein $R_2$, $R_3$, $R_4$, $R_5$ and $m$ are as defined hereinbefore. That process is exemplified by the reaction of methyl 2-methoxy-4-hydroxy-5-oxocyclopent-1-eneheptanoate, the preparation of which starting material is described in Example 8 of the aforementioned U.S. Pat. No. 3,558,682, with lithium tetra-[3-(tetrahydropyran-2-yloxy)-4,4-dimethyl-1-octynyl]aluminate to afford, after hydrolysis of the organometallic adduct with hydrochloric acid, 7-[3-(RS)-hydroxy-2-(3(RS)-hydroxy-4,4-dimethyl-1-octynyl)-5-oxocyclopent-1-ene]heptanoic acid. Manufacture of a monoalkyl derivative is typified by the substitution of lityium tetra-[3-(tetrahydropyran 2-yloxy)-4-methyl-1-octynyl]aluminate in the latter process to afford 7-[3(RS)-hydroxy-2-(3(RS)-hydroxy-4-methyl-1-octynyl)-5-oxocyclopent-1-ene]heptanoic acid.

The acetylenic alcohol intermediates are produced by reaction of the appropriate carbonyl compounds with an organometallic acetylene reagent, e.g. acetylene magnesium bromide. Typically, 2,2-dimethyl-n-hexaldehyde is contacted with acetylene magnesium bromide and the adduct hydrolyzed to afford 4,4-dimethyl-1-octyn-3-ol. The acetylenic alcohols in which the alcohol group is tertiary are obtained from the appropriate ketones. 2,2-Dimethyl-n-hexaldehyde, for example, is converted to 3,3-dimethyl-2-heptanone by reaction with methyl magnesium bromide followed by hydrolysis of the adduct and oxidation of the secondary alcohol group with chrominum trioxide. That ketone is then contacted with acetylene magnesium bromide and the adduct hydrolyzed to afford 3,4,4-trimethyl-1-octyn-3-ol.

The lower alkyl carboxylic acid esters of this invention are readily obtained by esterification of the corresponding acids. Typically, 7-[3(RS)-hydroxy-2-(3(RS)-hydroxy-4,4-dimethyl-1-octynyl)-5-oxocyclopent-1-ene]heptanoic acid is contacted with ethereal diazo= methane, thus affording methyl 7-[3(RS)-hydroxy-2-(3(RS)-hydroxy-4,4-dimethyl-1-octynyl)-5-oxocyclopent-1-ene]= heptanoate.

Those compounds of this invention which possess an olefinic carboxylic acid side-chain are readily produced by utilizing the appropriate cyclopentenealkenoic acids, the preparations of which are described in pending Bruhn & Pappo U.S. patent application Ser. No. 346,358, filed Mar. 30, 1973. Methyl 7-(2-methoxy-4-hydroxy-5-oxocyclopent-1-ene)hept-5-cis-enoate, whose manufacture is described in the latter patent application, is contacted with lithium tetra-[3-(tetrahydropyran-2-yloxy)-4,4-dimethyl-1octynyl]aluminate to produce 7-[3(RS)-hydroxy-2-(3(RS)-hydroxy-4,4-dimethyl-1-octynyl)-5-oxocyclopent-1ene]hept-5-cis-enoic acid.

The instant compounds containing a tertiary alcohol group in the alkynyl side-chain are produced by reaction of the cyclopentene carboxylic acid intermediates with the organometallic derivative of an acetylenic alcohol, or the hydroxy protected derivative thereof, as represented by the following structural formula

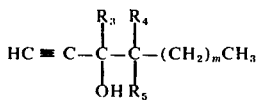

wherein $R_3$ is a lower alkyl radical and $R_4$, $R_5$ and m are as hereinbefore defined. A specific example is the reaction of methyl 7-(2-methoxy-4-hydroxy-5-oxocyclopent-1-ene)heptanoate with lithium tetra-[3-(tetrahydropyran-2-yloxy)-3,4,4-trimethyl-1-octynyl]aluminate to produce 7[3-hydroxy-2-(3-hydroxy-3,4,4-trimethyl-1-octynyl)-5-oxocyclopent-1-ene]heptanoic acid.

The optically active dextrorotatory and levorotatory derivatives of this invention are obtained by utilizing, as intermediates, the appropriate optically active acetylenic alcohols. For example, 4,4-dimethyl-1-octyn-3-ol is converted to the phthalic acid half-ester by reaction with phthalic anhydride and the half-ester is reacted with (—)α-methybenzylamine to afford the diastereomeric salts, which are separated by fractional crystallization, then hydrolyzed to afford the individual R and S acetylenic alcohols. Resolution of the final products is achieved by reaction with an optically active carbonyl reagent, followed by cleavage of the resulting derivative.

For example, methy 7-[3(RS)-hydroxy-2-(3(S)-hydroxy-4,4-dimethyl-1-octynyl)-5-oxocyclopent-1-ene]= heptanoate is contacted with 2(S)-aminoxyisocaproic acid to afford methyl 7-[3(R)-hydroxy-2-(3(S)-hydroxy-4,4-dimethyl1 1-octynyl)-5-(1carboxyisoamyl)oximino]cyclopent-1-eneheptanoate and methyl 7-[3(S)-hydroxy-2-(3(S)-hydroxy-4,4-dimethyl-1-octynyl)-5-(1-carboxyisoamyl)oxyimino]= cyclopent-1-eneheptanoate, which are separated chromatographically. Hydrolysis of those oximes with aqueous titanium trichloride affords methyl 7-[3(R)-hydroxy-2-(3(S)-hydroxy-4,4-dimethyl-1-octynyl)-5-oxocyclopent-1-ene]heptanoate and methyl 7-[3(S)-hydroxy-2-(3(S)-hydroxy-4,4-dimethyl-1-octynyl)-5-oxocylopent-1-ene]heptanoate.

The instant compounds which lack a hydroxy group in the alkynyl side-chain are obtained by utilizing the appropriate alkynyl organometallic intermediate. Lithium tetra-(4,4-dimethyloctynyl)aluminate thus is condensed, by the procedure described hereinbefore, with methyl 2-methoxy-4-hydroxy-5-oxocyclopent-1-heptanoate to afford 7-[3-hydroxy-2-(4,4-dimethyl-1-octynyl)-5-oxocylopent-1-ene]heptanoic acid.

The instant compounds containing a cycloalkyl group in the alkynyl side-chain are produced by utilizing the appropriate acetylenic alcohol organometallic derivative. For example, lithium tetra-[3-(tetrahydropyran-2-yloxy)-3-(1-butylcyclohexyl)-1-ethynyl-]aluminate is allowed to react with methyl 7-(2-methoxy-4-hydroxy-5-oxocyclopent-1-ene)heptanoate to afford 7-[3-hydroxy-2-(3-hydroxy-3-(1-butylcyclohexyl)-1-ethynyl)-5-oxocyclopent-1-ene]= heptanoic acid. The acetylenic alcohol intermediate is produced by forming the cyclohexylimine of cyclohexane=carboxaldehyde, alkylating that imine with n-butyl iodide, hydrolyzing the product and reacting the resulting 1-butylcyclohexane carboxaldehyde with acetylene magnesium bromide to afford 3-(1-butylcyclohexyl)-1-ethyn-3-ol. In similar fashion, 2-n-butylcyclohexanone is converted to 2-n-butyl-1-ethynylcyclohexanol. Conversion of that alcohol to the tetrahydropyranyl ether, then to the lithium aluminate derivative and reaction of the latter organometallic intermediate with, for example, methyl 7-(2-methoxy-4-hydroxy-5-oxocyclopent-1-ene)heptanoate yields 7-[3-hydroxy-2-[(2-n-butyl-1-hydroxycyclohexyl)-1-ethynyl]-5-oxocyclopent-1-ene]heptanoic acid.

The novel compounds of this invention exhibit valuable pharmacological properties, as is evidenced by their ability to inhibit the gastric secretion stimulatory properties of secretogogues such as histamine and pentagastrin.

Following is a description of the specific assay procedure:

Adult female beagle dogs weighing 4.5–7.3 kg. are equipped with a telfon-stainless gastric cannula implanted in the most dependent portion of the stomach near the antrum. After a recovery period of 1 month following surgery, the animals are fasted for approximately 20 hours, then are placed in a leather sling permitting only limited movement. The gastric cannula is opened and cleansed with warm (37°C.) saline solution. The dogs are injected with either of two secretogogues, histamine or pentagastrin, at a dose approximately equal to ⅔ of that which will effect maximal stimulation. Immediately thereafter the test compound dissolved in iso-osmotic buffer solution is administered subcutaneously. The gastric juice is collected for a period of 2 hours following administration of the secretogogue and the total volume is measured. These results are compared with those obtained from control dogs treated with the secretogogue alone. A compound is rated active if statistically significant inhibition of secretory parameters occur following compound treatment.

The invention will appear more fully from the example which follow. These examples are given by way of illustration only and are not to be construed as limiting the invention either in spirit or in scope as many modifications both in materials and methods will be apparent from this disclosure to those skilled in the art. In these examples temperatures are given in degrees Centigrade (°C.) and quantities of materials in parts by weight unless otherwise noted.

EXAMPLE 1

14.85 Parts of 5-chloropent-1-yne is dissolved in 250 parts by volume of toluene and the resulting solution is cooled to approximately —40°. To that solution is then added 62.8 parts by volume of 2.31 M ethereal butyl lithium and stirring is continued for approximately 15 minutes. 6.87 Parts of boron trifluoride etherate is added and the reaction mixture is stirred for about 2 hours, then allowed to stand for about 16 hours at —5° to —10°. At the end of that time 10.14 parts of methyl vinyl ketone is added at —40° and the reaction mixture is stirred for about 4 hours, then is quenched with water. 50 Parts by volume of 3 N hydrochloric acid is added and the mixture is kept at room temperature for about 16 hours, at the end of which time the aqueous and organic layers are separated. The aqueous layer is extracted with toluene and the organic layer with water. The organic solutions are combined, washed successively with aqueous sodium hydroxide and water, then dried over anhydrous sodium sulfate and stripped to dryness under reduced pressure, thus affording the crude product. This material is purified by distillation under reduced pressure to afford 9-chloro-5-nonyn-2-one, boiling at about 80°–92° at a pressure of 0.11–0.06 mm.

EXAMPLE 2

To a solution consisting of 2.77 parts of 9-chloro-5-nonyn-2-one in 8 parts by volume of ethanol is added a solution containing 2.77 parts of sodium cyanide dissolved in 4 parts of water. The resulting reaction mixture is heated at 80°–100° for abut 24 hours, then is cooled and diluted with ether, whereupon 20 parts by volume of dilute aqueous sodium hydroxide is added with stirring. The layers are separated and the alkaline layer extracted with ether. The ether extracts are combined, then washed with water, dried over anhydrous sodium sulfate and concentrated under reduced pressure to afford 9-cyano-5-nonyn-2-one. This compound exhibits an infrared absorption maximum at 2250 reciprocal centimeters and nuclear magnetic resonance peaks at $\delta 2.18$ and $\delta 2.50$.

EXAMPLE 3

A mixture consisting of 1.79 parts of 9-cyano-5-nonyn-2-one, 5 parts by volume of ethanol and 5 parts by volume of 5% aqueous sodium hydroxide is heated just below the reflux temperature for about 6 hours, then is cooled and extracted with chloroform. The alkaline layer is acidified by means of hydrochloric acid to pH 4, resulting in separation of a brown liquid. This material is extracted with chloroform and the chloroform solution is washed with water, dried over anhydrous sodium sulfate, then concentrated to dryness under reduced pressure to afford 9-oxo-5-decynoic acid. It exhibits nuclear magnetic resonance peak at $\beta 2.18$ and $\beta 2.50$.

EXAMPLE 4

To a solution of 23.6 parts of 9-oxo-5-cis-decynoic acid in a mixture of 999 parts by volume of benzene and 221.4 parts by volume of 1% quinoline in benzene is added 1.18 parts of 5% palladium-on-barium sulfate catalyst and the resulting mixture is shaken with hydrogen at atmospheric pressure and room temperature until one molecular equivalent of hydrogen is absorbed. The catalyst is then removed by filtration and the filtrate is washed successively with dilute hydrochloric acid and water, then dried over anhydrous sodium sulfate and stripped of solvent under reduced pressure, thus producing 9-oxo-5-cis-decenoic acid, which exhibits nuclear magnetic resonance maxima at $\delta 2.13$ and $\delta 5.39$.

EXAMPLE 5

A solution of potassium tertiary-butoxide is prepared by dissolving 4.8 parts of potassium metal in 30 parts by volume of tertiary-butyl alcohol at reflux temperature under nitrogen. To that solution is then added a solution consisting of 3.7 parts of 9-oxo-5-cis-decenoic acid and 7.23 parts of dimethyl oxalate dissolved in 25 parts by volume of tertiary-butyl alcohol. The addition is conducted with stirring at the reflux temperature. After the reaction mixture is refluxed under nitrogen for about 2½ hours, the colored supernatant is decanted and the precipitate is dissolved in water, then acidified with dilute hydrochloric acid. Extraction of that acidic mixture with chloroform affords an organic solution, which is washed with saturated aqueous sodium chloride, then dried over anhydrous sodium sulfate and stripped of solvent under reduced pressure to afford 7-(2,3,5-trioxo-4-methoxalylcyclopentane)hept-5-cis-enoic acid, melting at about 99°–104°.

EXAMPLE 6

A mixture consisting of 10.6 parts of 7-(2,3,5-trioxo-4-methoxalylcyclopentane)hept-5-cis-enoic acid and 490 parts by volume of dilute hydrochloric acid is heated at the reflux temperature for about 3 hours, then is cooled and extracted with ethyl acetate. The organic extract is washed with saturated aqueous sodium chloride, then dried over anhydrous sodium sulfate and stripped of solvent under reduced pressure to afford the crude product. Purification of that material is effected by adsorption on a silicic acid chromatographic column followed by elution with ethyl acetate-benzene. From the eluate there are obtained pale yellow crystals of 7-(2,3,5-trioxocyclopentane)hept-5-cis-enoic acid, melting at about 84°–85°.

EXAMPLE 7

A solution of 0.54 part of 7-(2,3,5-trioxocyclopentane)hept-5-cis-enoic acid in 11 parts of water is neutralized by the addition of dilute aqueous sodium hydroxide and that neutralized solution is cooled to 0°–5°, at which point 0.037 part of sodium borohydride is added. The reaction mixture is stirred at 0°–5° for about 50 minutes, then is quenched by the addition of dilute hydrochloric acid to pH 1. The resulting solution is extracted several times with ethyl acetate. The ethyl acetate extracts are combined, washed with saturated aqueous sodium chloride, dried over anhydrous sodium sulfate and concentrated to dryness under reduced pressure to afford white crystals of 7-(2,5-dioxo-3-hydroxycyclopentane)hept-5-cis-enoic acid, melting at about 83°–85°.

EXAMPLE 8

To a solution of 2.99 parts of 7-(2,5-dioxo-3-hydroxycyclopentane)hept-5-cis-enoic acid in 33.8 parts by volume of methanol, under nitrogen, is added, with stirring, 10.18 parts by volume of acetone dimethyl ketal followed by 3.97 parts by volume of 1.14% methanolic hydrogen chloride. The resulting reaction mixture is allowed to stand at room temperature for about 48 hours, then is stripped of solvent by distillation under reduced pressure. A small amount of ether is added and the mixture is allowed to stand for about 48 hours, then is dissolved in benzene containing 1% triethylamine and that solution is washed successively with dilute aqueous potassium carbonate and water, then dried over anhydrous sodium sulfate and stripped of solvent under reduced pressure to afford white crystals of methyl 7-(4-hydroxy-2-methoxy-5-oxocyclopent-1-ene)hept-5-cis-enoate, melting at about 77°–78°. It exhibits nuclear magnetic resonance maxima at $\delta 3.69$, $\delta 3.98$, $\delta 4.29$ and $\delta 5.39$.

EXAMPLE 9

To a solution of 0.256 part of methyl 7-(4-hydroxy-2-methoxy-5-oxocyclopent-1-ene)hept-5-cis-enoate in a mixture consisting of 3.7 parts by volume of tetrahydrofuran and 484 parts by volume of toluene, under nitrogen, is added, dropwise at −70°, 0.33 parts by volume of a 3.3 M sodium dihydro bis-(2-methoxyethoxyaluminate in benzene solution. Stirring is continued at that temperature for about 5½ hours, at the end of which time the reaction mixture is quenched by the addition of methanol. After an additional 10 minute stirring period, the mixture is allowed to warm to room temperature, then is acidified to pH 2 by the addition of dilute hydrochloric acid. The resulting two phase mixture is extracted with ethyl acetate and the organic extract is washed with saturated aqueous sodium chloride, then dried over anhydrous sodium sulfate and stripped of solvent under reduced pressure to afford the crude product. That material is purified by adsorption on a silicic acid chromatographic column followed by elution with ethyl acetate in benzene to afford, as an oil, methyl 7-(3-hydroxy-5-oxocyclopent-1-ene)hept-5-cis-enoate. It exhibits nuclear magnetic resonance maxima at δ3.68, δ5.57 and δ7.19.

EXAMPLE 10

To a solution of 0.288 part of methyl 7-(3-hydroxy-5-oxocyclopent-1-ene)hept-5-cis-enoate in 3.6 parts by volume of ether is added 0.01 part of p-toluenesulfonic acid and 0.109 part of dihydropyran. The reaction mixture is allowed to stand at room temperature for about 24 hours, then is diluted with water, washed successively with 5% aqueous potassium carbonate and water, dried over anhydrous sodium sulfate and stripped of solvent under reduced pressure. The resulting product is methyl 7-(3-tetrahydropyran-2'-yloxy-5-oxocyclopent-1-ene)hept-5-cis-enoate.

EXAMPLE 11

To a solutionn of 1.82 parts of 9-oxo-5-decynoic acid in 40 parts by volume of 50% aqueous ethanol is added 0.53 part of anhydrous sodium carbonate and the resulting solution is concentrated to dryness under reduced pressure. The residue is thoroughly dried, then is mixed with 200 parts by volume of anhydrous ammonia and that mixture is stirred vigorously at approximately −70° while 0.46 part of sodium metal is added in small portions. When the absence of unreacted sodium is indicated by disappearance of the characteristic blue color, the ammonia is removed under an atmosphere of nitrogen and dilute hydrochloric acid is added to the residue. That acidic mixture is extracted with benzene and the benzene extracts are combined, washed with water, dried over anhydrous sodium sulfate and stripped of solvent under reduced pressure to afford 9-oxo-5-trans-decenoic acid.

EXAMPLE 12

When 0.14 part of lithium metal is substituted for sodium metal in the procedure of Example 11, 9-oxo-5-trans-decenoic acid is, similarly, obtained.

EXAMPLE 13

To a solution of 0.238 part of methyl 7-(3-hydroxy-5-oxocyclopent-1-ene)hept-5-cis-enoate in 4 parts by volume of isopropyl alcohol is added a solution consisting of 0.04 part of sodium hydroxide in 1 part of water and the resulting reaction mixture is allowed to stand, in an atmosphere of nitrogen, at 0°–5° for about 16 hours. At the end of that time the reaction mixture is acidified by the addition of 1.1 parts by volume of 1 N hydrochloric acid, then is concentrated to a small volume at room temperature under reduced pressure. Extraction of that acidic mixture with ethyl acetate affords an organic solution, which is washed with aqueous sodium chloride, dried over anhydrous sodium sulfate and evaporated to dryness under reduced pressure, thus affording the crude product. Purification of that substance is effected by adsorption on a silicic acid chromatographic column followed by elution with ethyl acetate in benzene, thus affording 7-(3-hydroxy-5-oxo=cyclopent-1-ene)hept-5-cis-enoic acid.

EXAMPLE 14

A mixture consisting of 144 parts of isobutyr=aldehyde, 198 parts of cyclohexylamine and 200 parts by volume of benzene is heated at the reflux temperature and the water of reaction is collected by means of a water trap. Reflux is continued until the separation of water ceases. The solvent is then removed by distillation under reduced pressure and the residue is distilled to afford N-cyclohexylisobutylideneimine, boiling at about 95°–100° at a pressure of about 3 mm. To 153 parts of ethyl magnesium bromide dissolved in approximately 500 parts of tetrahydrofuran is added, dropwise, N-cyclohexylisobutylideneimine and the resulting mixture is heated at reflux until the evolution of gas ceases. The mixture is cooled and 184 parts of n-butyl iodide is added dropwise with stirring. The mixture is heated at the reflux temperature for 5 to 6 hours, then is cooled and treated dropwise with 150 parts of concentrated hydrochloric acid dissolved in 400 parts of water. That reaction mixture is heated at the reflux temperature for about 2 hours, then is cooled and diluted with a mixture of ether and water. The ether layer is separated, washed with water, dried over anhydrous sodium sulfate and stripped of solvent under reduced pressure, thus affording 2,2-dimethyl-n-hexaldehyde, boiling at 33°–39° at a pressure of about 3 mm.

EXAMPLE 15

To a solution containing 90 parts of acetylene dissolved in 600 parts by volume of tetrahydrofuran is added, over a period of about 50 minutes at −70°, 600 parts by volume of tetrahydrofuran containing 133 parts of ethyl magnesium bromide. Acetylene gas is continuously passed through the mixture during the addition period. Following that addition, the mixture is stirred at approximately −40° for about 45 minutes. To that mixture is then added, with stirring under nitrogen over a period of about 1 hour, 80 parts by volume of 2,2-dimethyl-n-hexaldehyde dissolved in 350 parts by volume of tetra=hydrofuran. Stirring at room temperature is continued for about 16 hours, at the end of which time approximately 125 parts by volume of saturated aqueous ammonium chloride is added slowly with stirring. The precipitate which forms is removed by filtration and the filtrate is partially concentrated, then diluted with ether and again filtered. The filtrate is stripped of solvent, then is distilled under reduced pressure to afford 4,4-dimethyl-1-octyn-3-ol, boiling at about 55°–65° at a pressure of about 3 mm.

EXAMPLE 16

To a solution of 58 parts of 4,4-dimethyl-1-octyn-3-ol in 116 parts by volume of dry benzene is added first 158 parts of tetrahydropyran then, with cooling, 0.29 part of p-toluenesulfonic acid. The reaction mixture is stored at room temperature for about 16 hours, then is diluted with benzene and washed successively with dilute aqueous sodium hydroxide and water. Drying over anhydrous sodium sulfate followed by removal of the solvent under reduced pressure affords 4,4-dimethyl-1-octyn-3-ol tetrahydropyran-2-yl ether.

EXAMPLE 17

A solution consisting of 38 parts of 4,4-dimethyl-1-octyn-3-ol tetrahydropyran-2-yl ether in 300 parts of tetrahydrofuran is cooled to approximately −40° and 70 parts by volume of 2.2 M butyl lithium in hexane is added over a period of about 2 minutes. The resulting mixture is stirred for approximately 10 minutes at about −40°, then at room temperature for about 1 hour. The mixture is then cooled to −40° and 5.36 parts of aluminum chloride is added over a period of about 15 minutes. Stirring is continued at room temperature for about 90 minutes. To that reaction mixture is then added 9.72 parts of methyl 2-methoxy-4-hydroxy-5-oxocy=clopent-1-eneheptanoate dissolved in 100 parts by volume of tetrahydrofuran. The addition is carried out at room temperature over a period of approximately 30 minutes. Stirring at room temperature is continued for approximately 2½ hours, at the end of which time the mixture is acidified by the addition of dilute hydrochloric acid. The solvent is removed by evaporation at room temperature and the residue is extracted into ethyl acetate. The ethyl acetate extract is washed with water, then concentrated to dryness under reduced pressure. The resulting residue is dissolved in a mixture consisting of 175 parts by volume of methanol and 20 parts by volume of 1 N hydrochloric acid. That mixture is kept at 30°–35° for approximately 6 hours and the methanol is then removed by distillation under reduced pressure. The resulting residue is extracted into ethyl acetate and the organic layer is washed with water, then extracted several times with dilute aqueous potassium bicarbonate. The alkaline extracts are acidified with hydrochloric acid, then extracted with ethyl acetate. The organic extract is washed with water, then concentrated to dryness under reduced pressure. The ethyl acetate solution containing the neutral fraction is concentrated to dryness under reduced pressure and the residue is dissolved in approximately 250 parts by volume of methanol. The solution is mixed with 100 parts by volume of 5% aqueous potassium carbonate and that mixture is allowed to stand at room temperature for about 18 hours. The methanol is then removed by distillation at room temperature and the resulting residue is diluted with a mixture of ether and benzene. The organic layer is separated, dried over anhydrous sodium sulfate and concentrated to dryness under reduced pressure. The alkaline layer is acidified with hydrochloric acid, then extracted with ethyl acetate. The organic layer is separated, washed with water, dried over anhydrous sodium sulfate and concentrated under reduced pressure to afford a residue which is purified by adsorption on a silicic acid chromatographic column followed by elution with 5% ethyl acetate in benzene to afford 7-[3(RS)-hydroxy-2-(3(RS)-hydroxy-4,4-dimethyl-1-octynyl)-5-oxocyclopent-1-ene]heptanoic acid.

EXAMPLE 18

When an equivalent quantity of 2-ethyl-n-butyraldehyde is substituted in the procedure of Example 14, there is produced 2,2-diethyl-n-hexaldehyde.

EXAMPLE 19

The substitution of an equivalent quantity of 2,2-diethyl-n-hexaldehyde in the procedure of Example 15 results in 4,4-diethyl-1-octyn-3-ol.

EXAMPLE 20

By substituting an equivalent quantity of 4,4-diethyl-1-octyn-3-ol in the procedure of Example 16, there is produced 4,4-diethyl-1-octyn-3-ol tetrahydropyran-2-yl ether.

EXAMPLE 21

The substitution of an equivalent quantity of 4,4-diethyl-1-octyn-3-ol tetrahydropyran-2-yl ether in the procedure of Example 17 affords 7-[3(RS)-hydroxy-2-(3(RS)-hydroxy-4,4-diethyl-1-octynyl)-5-oxocyclopent-1-ene]heptanoic acid.

EXAMPLE 22

To a mixture consisting of 7 parts of potassium hydroxide dissolved in 13 parts of water and 100 parts by volume of ether is added 6 parts of N-nitrosomethylurea. The resulting mixture is stirred until most of the solid is dissolved and the yellow ethereal solution is decanted into a solution consisting of 1 part of 7-[3(RS)-hydroxy-2-(3(RS)-hydroxy-4,4-dimethyl-1-octynyl)-5-oxocyclopent-1-ene]heptanoic acid dissolved in 50 parts by volume of cold methanol. The reaction mixture is allowed to stand at that temperature for several minutes, at the end of which time the excess reagent is destroyed by the dropwise addition of glacial acetic acid. When the ether solution becomes colorless, it is washed successively with cold water, cold dilute aqueous sodium bicarbonate and cold water, then dried over anhydrous sodium sulfate and concentrated to dryness under reduced pressure. The product thus obtained is further purified by adsorption on a silicic acid chromatographic column followed by elution with ethyl acetate in benzene mixtures, thus affording methyl 7-[3(RS)-hydroxy-2-(3-(RS)-hydroxy-4,4-dimethyl-1-octynyl)-5-oxocyclopent-1-ene]heptanoate.

EXAMPLE 23

A mixture consisting of 25 parts of 7-[3(RS)-hydroxy-2-(3(RS)-hydroxy-4,4-dimethyl-1-octynyl)-5-oxocyclopent-1-ene]heptanoic acid, 10 parts of acetic anhydride and 10 parts of pyridine is allowed to stand at room temperature for about 16 hours, then is poured carefully into cold excess aqueous citric acid. The resulting aqueous mixture is allowed to stand at room temperature for about one hour, then is extracted several times with ether. The combined ether extracts are washed with cold water, dried over anhydrous sodium sulfate and concentrated under reduced pressure. The resulting residue is purified by adsorption on a silicic acid chromatographic column followed by elution with ethyl acetate in benzene mixtures, thus affording 7-[3(RS)-acetoxy-2-(3(RS)-acetoxy-4,4-dimethyl-1-octynyl)-5-oxocyclopent-1-ene]heptanoic acid.

EXAMPLE 24

The substitution of an equivalent quantity of 3,4,4-trimethyl-1-octyn-3-ol in the procedure in Example 17 results in 7-[3(RS)-hydroxy-2-(3(RS)-hydroxy-3,4,4-trimethyl-1-octynyl)-5-oxocyclopent-1-ene]heptanoic acid.

EXAMPLE 25

A mixture consisting of 1.54 parts of 4,4-dimethyl-1-octyn-3-ol, 1.5 parts of phthalic anhydride and 2 parts by volume of pyridine is heated at the reflux temperature under nitrogen for 4 hours, then cooled and diluted with ether. That solution is extracted with dilute aqueous sodium hydroxide and the alkaline extract is washed with ether, then acidified with dilute hydrochloric acid and extracted with ether. The organic extract is washed with water, dried over anhydrous sodium sulfate and stripped of solvent. The resulting residue is triturated with hexane to afford 2-ethynyl-3,3-dimethyl-n-hexyl phthalate, melting at 57°–59°.

To a solution of 1.9 parts of 2-ethynyl-3,3-dimethyl-n-hexyl phthalate in 5 parts by volume of methylene dichloride is added 0.762 part of (—)α-methylbenzylamine. After a few minutes the solvent is removed by distillation and the residue is triturated with hexane, then recrystallized from hexane:ether (5:1) to afford the (—)α-methylbenzylamine salt of 2-ethynyl-3,3-dimethyl-n-hexyl phthalate, which exhibits an optical rotation, in chloroform, of −34.1°. A solution consisting of 2.5 parts of the latter amine salt, 20 parts by volume of 1 N sodium hydroxide and 20 parts by volume of methanol is heated at 60°–70° for 1 hour, then is diluted with hexane. The organic layer is separated, washed successively with water, 1 N hydrochloric acid and water, then dried over anhydrous sodium sulfate and concentrated to dryness to afford 4,4-dimethyl-1-octyn-3(R)-ol, which exhibits an optical rotation, in ether, of −12.2°.

What is claimed is:
1. A compound of the formula

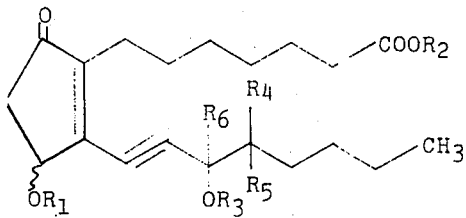

wherein $R_1$ and $R_3$ are hydrogen or a lower alkanoyl radical, $R_2$ and $R_6$ are hydrogen or a lower alkyl radical, $R_4$ and $R_5$ are lower alkyl radicals and the wavy line indicates the alternative R and S stereochemical configuration.

2. As in claim 1, a compound of the formula

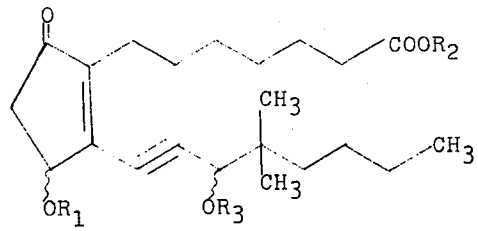

wherein $R_1$ and $R_3$ are hydrogen or a lower alkanoyl radical and $R_2$ is hydrogen or a lower alkyl radical.

3. As in claim 1, a compound of the formula

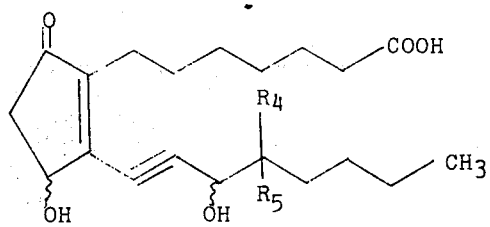

wherein $R_4$ and $R_5$ are lower alkyl radicals.

4. As in claim 1, the compound which is 7-[3(RS)-hydroxy-2-(3(RS)-hydroxy-4,4-dimethyl-1-octynyl)-5-oxocyclopent-1-ene]heptanoic acid.

5. As in claim 1, the compound which is 7-[3(R)-hydroxy-2-(3(RS)-hydroxy-4,4-dimethyl-1-octynyl)-5-oxocyclopent-1-ene]heptanoic acid.

6. As in claim 1, the compound which is 7-[3(R)-hydroxy-2(3(S)-hydroxy-4,4-dimethyl-1-octynyl)-5-oxocyclopent-1-ene]heptanoic acid.

7. As in claim 1, the compound which is 7-[3(RS)-hydroxy-2-(3(S)-hydroxy-4,4-dimethyl-1-octynyl)-5-oxocyclopent-1-ene]heptanoic acid.

* * * * *

UNITED STATES PATENT OFFICE
CERTIFICATE OF CORRECTION

PATENT NO. : 3,932,496

DATED : January 13, 1976

INVENTOR(S) : Christopher Jung and Raphael Pappo

Page 1 of 2

It is certified that error appears in the above-identified patent and that said Letters Patent are hereby corrected as shown below:

Column 1, line 53, "ethy" should read -- ethyl --.

Column 2, line 20, "lityium" should read -- lithium --.

Column 3, line 28, "methy" should read -- methyl --.

Column 3, line 33, "dimethyll" should read -- dimethyl-l --.

Column 4, line 15, "telfon" should read -- teflon --.

Column 4, line 15, "stainless" should read -- stainless steel --.

Column 4, lines 35 and 36, "example" should read --examples --.

Column 5, line 34, "β2.18 and β2.50" should read -- δ2.18 and δ2.50 --.

Column 6, line 62, "484" should read -- 4.4 --.

Column 7, line 29, "solutionn" should read -- solution --.

Continued..........

UNITED STATES PATENT OFFICE
CERTIFICATE OF CORRECTION

PATENT NO. : 3,932,496

DATED : January 13, 1976

INVENTOR(S) : Christopher Jung and Raphael Pappo

It is certified that error appears in the above-identified patent and that said Letters Patent are hereby corrected as shown below:

Column 2, lines 4-8, formula

" 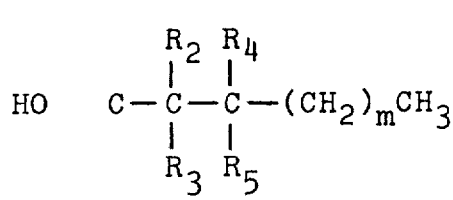 "

should read

-- 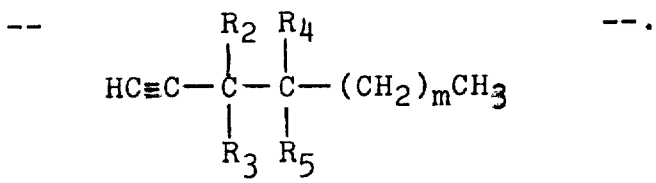 --.

Signed and Sealed this

*twenty-fifth* Day of *May 1976*

[SEAL]

Attest:

RUTH C. MASON
*Attesting Officer*

C. MARSHALL DANN
*Commissioner of Patents and Trademarks*